United States Patent [19]
Lipton

[11] Patent Number: 5,944,720
[45] Date of Patent: Aug. 31, 1999

[54] POSTERIOR SPINAL FIXATION SYSTEM

[76] Inventor: Glenn E Lipton, 2 Ashwood La., Trooper, Pa. 19403

[21] Appl. No.: 09/047,580

[22] Filed: Mar. 25, 1998

[51] Int. Cl.[6] .................................................. A61B 17/70
[52] U.S. Cl. .............................................. 606/61; 606/72
[58] Field of Search .................. 606/61, 60, 72, 606/73, 101; 623/17

[56] References Cited

U.S. PATENT DOCUMENTS

| | | | |
|---|---|---|---|
| 5,074,864 | 12/1991 | Cozad et al. | 606/61 |
| 5,102,412 | 4/1992 | Rogzinski | 606/61 |
| 5,112,332 | 5/1992 | Cozad et al. | 606/61 |
| 5,116,334 | 5/1992 | Cozad et al. | 606/61 |
| 5,147,359 | 9/1992 | Cozad et al. | 606/61 |
| 5,154,718 | 10/1992 | Cozad et al. | 606/61 |
| 5,246,442 | 9/1993 | Ashman et al. | 606/61 |
| 5,257,993 | 11/1993 | Asher et al. | 606/61 |
| 5,261,913 | 11/1993 | Marnay | 606/61 |
| 5,263,954 | 11/1993 | Schlapfer et al. | 606/61 |
| 5,281,222 | 1/1994 | Allard et al. | 606/54 |
| 5,334,203 | 8/1994 | Wagner | 606/61 |
| 5,346,493 | 9/1994 | Stanhurski et al. | |
| 5,380,325 | 1/1995 | Lahille et al. | 606/61 |
| 5,380,326 | 1/1995 | Lin | 606/61 |
| 5,382,248 | 1/1995 | Jacobson et al. | 606/61 |
| 5,389,099 | 2/1995 | Hartmeister et al. | 606/61 |
| 5,403,315 | 4/1995 | Ashman | 606/61 |
| 5,415,659 | 5/1995 | Lee et al. | 606/61 |
| 5,476,462 | 12/1995 | Allard et al. | 606/61 |
| 5,527,314 | 6/1996 | Brumfield et al. | 606/61 |

(List continued on next page.)

FOREIGN PATENT DOCUMENTS

WO 93/21848   11/1993   WIPO .

OTHER PUBLICATIONS

Journal of Bone and Joint Surgery, 1953, Richards Manufactur. Jewett, vol. 35 A, p. 3.

CD Horizon Spinal System Surgical Tech. Guide, 1997, Laufer and Bowe Sofamor Danek, pp. 4 to 25.

Universal Spinal System. Surg. Tech. Guide for Scoliosis, 1994, Synthes Spine, pp. 1 to 15.

Surgical Tech. for Isola Idiopathic Scoliosis Instrumentation, 1997, Asher Acromed, pp. 2 to 7.

*Primary Examiner*—Guy V. Tucker
*Attorney, Agent, or Firm*—Jeffrey C. Lew

[57] ABSTRACT

This invention relates to segmental spinal instrumentation, specifically metal spinal hooks and rods used for the correction of spinal deformities such as idiopathic scoliosis. It includes an apparatus for use in retaining a longitudinally extending member in position relative to a spinal column. The apparatus is comprised of a body having an open ended recess which extends through the body and is open along one side to enable the longitudinally extending member, spinal rod, to be moved into the recess. The recess having a side opening, a first end opening formed in a first side of the body and intersecting the side opening, and a second end opening formed in a second side of the body opposite from the first side and intersecting the side opening to enable the longitudinally extending member to be moved into the recess through the side opening and to extend from the first and second sides of the body through the first and second end openings. The recess having an inner thread convolution to enable receipt of fastener. The body including first and second ridges disposed on opposite sides of said side opening to enable engaging of reduction instrument. A connector element extending from a side of said body opposite from the side opening and connectable with the spinal column to connect said body with the spinal column. An apparatus is used for reducing a longitudinal member into hook body recess, said apparatus comprising a handle which extends to hook shaped configurations which engage ridges on hook body allowing reduction of longitudinal member through lever action.

5 Claims, 8 Drawing Sheets

U.S. PATENT DOCUMENTS

| | | | |
|---|---|---|---|
| 5,534,002 | 7/1996 | Brumfield et al. | 606/61 |
| 5,562,662 | 10/1996 | Brumfield et al. | 606/61 |
| 5,609,592 | 3/1997 | Brumfield et al. | 606/61 |
| 5,611,800 | 3/1997 | Davis et al. | 606/61 |
| 5,630,817 | 5/1997 | Rokegem et al. | 606/61 |
| 5,643,260 | 7/1997 | Doherty | 606/61 |
| 5,676,665 | 10/1997 | Bryan | 606/61 |
| 5,676,703 | 10/1997 | Gelbard | 623/17 |
| 5,681,319 | 10/1997 | Biedermann et al. | 606/61 |
| 5,688,273 | 11/1997 | Errico et al. | 606/61 |
| 5,688,274 | 11/1997 | Enrico et al. | 606/61 |

POSTERIOR SPINAL FIXATION SYSTEM

BACKGROUND

1. Field of Invention

The management of spinal deformities has undergone major changes in the past decade, especially with the introduction of the multi-hooked segmental rigid fixation devices that have entered the market. This invention relates to segmental spinal instrumentation, specifically metal spinal hooks and rods used for the correction of spinal deformities such as idiopathic scoliosis.

2. Description of Prior Art

Several spinal implant systems currently exist on the market today. Many of these systems demonstrate deficiencies related to the manner of connecting the rod to the spinal hooks used in the spinal fixation system. The main advantage of the present spinal system is the ease in reducing the spinal rod to the hooks, thus saving time in the operating theater. Some problems with prior systems are found when inserting the hook and rod constructs. There are many parts and many steps in the assembly of those parts. The numerous parts and steps leads to additional time spent in the operating theater leading to increased morbidity for the patient and increased operating expense. The present invention both simplifies and reduces the number of steps effectively lessening the time spent in the operating theater, in that the spinal hooks and tool used during the operation have been redesigned. Specifically, the hooks and tool used for reducing the rod to the hook for placement of the set screw to secure the rod in place have been redesigned. Previous systems illustrate elaborate methods for reduction of the rod to the hook when the distance is greater than approximately 0.5 inch. For example, one spinal implant system teaches the surgeon he should use three tools for the reduction when he is unable to reduce the rod because it remains at a distance too great to use a screwdriver alone. First, the hook is secured with a clamp encompassing the hook and rod; this also obscures the view of where the set screw is placed. A second device is attached to the side of the first device and is braced against the rod. A third device, identical to the second device, is attached to the opposite side of the first device and is braced against the rod. Using a screw method, the second and third devices are turned clockwise, advancing a screw mechanism which pushes the rod down to the secured hook. After the rod is seated the set screw is placed on the hook through the top of the first device that is hollowed out for set screw placement. Finally, the second and third devices are unscrewed and removed, and the first device is unclamped and removed after which the next hook may be reduced.

Other spinal hook and rod systems have the same problem as illustrated above with more complicated methods of securing the rod to the hook.

Specifically, another spinal hook and rod system requires additional steps after a similar reduction of the rod to the hook. To place the securing set screw, another device is required to position an end cap, which contains the set screw, partially on the hook. This first device is then removed and a second device is placed to push the end cap fully on the hook. This device is then removed and finally the set screw may be tightened after the end cap containing the set screw is correctly positioned. This clearly demonstrates difficulties encountered with this system and highlights the need for multiple instruments in the insertion and procurement of fixation of the rod and hooks.

Another different spinal system includes many instruments for the insertion of the device. Additionally, many extra steps are required to use these instruments. Specifically, to reduce the rod to the hook special rod-introduction pliers are used. The pliers must be pre-loaded with a collar. These pliers are then placed over a protruding pin which is attached to the hook. The pliers then engage the rod and align the hook and rod. Then another tool is used to release the collar which temporarily retains the rod. After the pliers are removed a nut is placed to permanently secure the collar to the hook.

Other spinal implant systems currently existing on the market today exhibit the same, similar or greater disadvantages including but not limited to those described above. Additional disadvantages of the existing spinal hook and rod systems are realized by recognizing the need to remove and replace the hooks and rods in surgical patients. Many of the steps of placement must be reversed to remove or reset the rods and hooks, adding time to the procedure. Further, The manufacturing of the hooks with more parts generally presents difficulties with the complex machining. Additionally, the manufacturing of multiple, complex hooks and additional tools for insertion of the hooks requires extra machinery for high volume production.

OBJECTS AND ADVANTAGES

Several objects and advantages of the present invention are:

1. to reduce the time required to operate on patients undergoing posterior spinal fixation;
2. to reduce the number of tools required to operate on patients undergoing posterior spinal fixation;
3. to reduce the complexity of the operative process in patients undergoing posterior spinal fixation;
4. to simplify the process of connecting spinal hooks to rods;
5. to provide a spinal instrumentation system which is requires less resources to manufacture; and
6. to provide a spinal instrumentation system in which its operation is easily taught and learned.

DRAWING FIGURES

REFERENCES IN THE DRAWING

A Projecting metal ridges
B Open area of blade of thoracic lamina hook for spine engagement
B2 Open area of blade of pedicle hook for spine engagement
B3 Open area of blade of lamina hook for spine engagement
C Open area of body of spinal hook, receives rod
D flook shaped configuration on mating end of reduction tool
D2 Groove in blade of pedicle hook
E Open area of reduction tool, receives ridges of hook
F Open area of reduction tool, receives hook body
G Spinal hooks inserted into spine
H Set screw
I Screwdriver
J Spinal rod
K Tool for rod reduction Description—FIGS. 1 to 12

In all of the following drawings of spinal hooks the front of the hook begins on the side with the area described as the blade. The back of the hook begins on the side with the area described as the body. The top of the hook begins on the side with the part of the blade that projects past the body of the hook. The bottom of the hook is the side opposite to the top.

Figure 1:
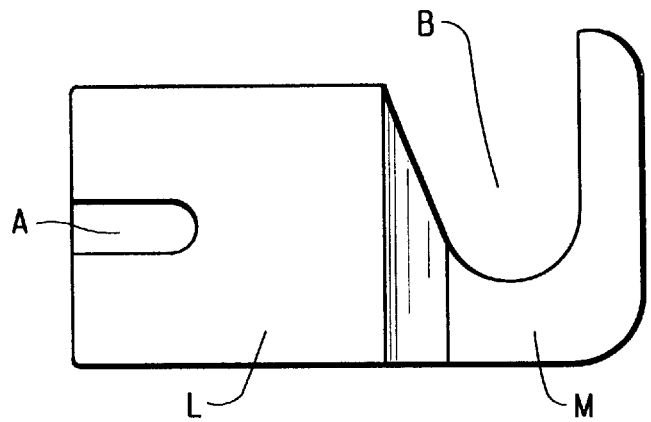
FIG. 1 shows a side view of a thoracic lamina spinal hook.

FIG. 1 shows a side view of a thoracic lamina hook used in the posterior spinal fixation system described in this patent application. The part of the thoracic lamina hook labeled L is the body of the spinal hook and is the area measured from the back of the hook forward 12 mm towards the front of the hook and from the bottom of the hook up 11 mm towards the top of the hook. In this side view a ridge (FIG. 1, label A) flush with the back and 4.5 mm from the bottom and 4.5 from the top, with a width of 2.0 mm and a length of 5.0 mm projects out of the page, with the front facing edge being rounded (1.0 mm radius). The body of this hook is the same for each subsequent hook described. The part of the thoracic lamina hook labeled M is the blade of the spinal hook and is the area measured from the front of the hook backwards 10.5 mm towards the back of the hook and ends where the body of the hook begins, and from the bottom of the hook up 13 mm towards the top of the hook. In this side view the open area (FIG. 1, label B) of the blade is seen having a depth of 7.5 mm, rounded at the bottom (radius 3.0 mm) with a slope from the hook body going down 4.5 mm and towards the front of the hook a distance of 2.0 mm. The bottom front of the blade is rounded (radius 3.5 mm) and the top front of the blade is rounded (radius 2.5 mm).

Figure 2:
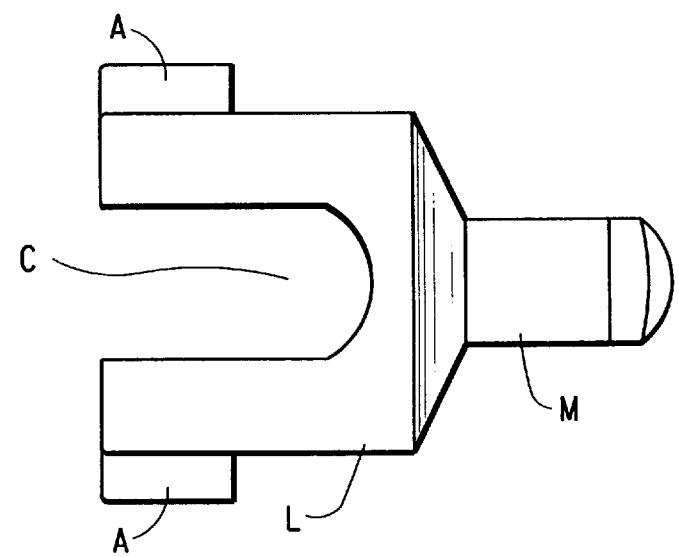
FIG. 2 shows a top view of a thoracic lamina spinal hook.

In FIG. 2 the top view of the thoracic lamina hook is illustrated. In this top view the body (FIG. 2, label L) of the hook is 18 mm measured from side to side by 12 mm measured from front to back. The ridge of metal (FIG. 2, label A) in this view is seen on both sides of the hook and measures 2.0 mm from side to side and 5.0 mm from back to front. In this side view the open area (FIG. 2, label C) of the body is seen having a depth of 11 mm measured back to front, and width 6.0 mm measured side to side, rounded at the bottom (radius 3.0 mm). The open area of the body is tapped from the back to the front (7.0 mm deep) for the placement of a 10 mm wide fine threaded screw. The width of the blade (FIG. 2, label M) is 5.0 mm measured side to side, with the front face of the blade being rounded, and the length is 10.5 mm with the blade enlarging from 5 mm to 14 mm at the site where the body of the hook begins.

Figure 3:
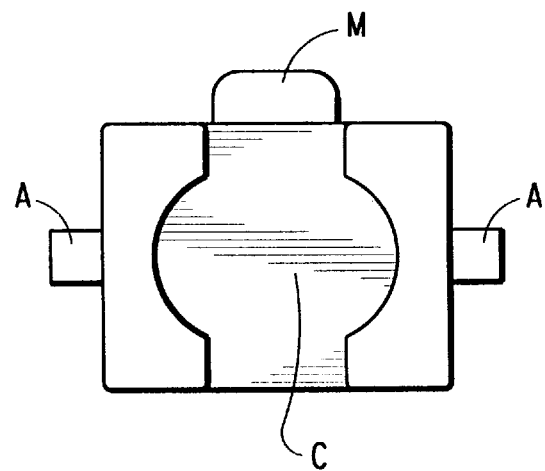
FIG. 3 shows a back view of a thoracic lamina spinal hook.

In FIG. 3 the back view of the thoracic lamina hook is illustrated. The body measured from the bottom to the top is 11.0 mm and the width measured from side to side is 18.0 mm. The 2.0 mm by 2.0 mm ridges (FIG. 3, label A) on this view are not rounded. The open area (FIG. 3, label C) of the body is seen and measures 6.0 mm in width at the top and bottom of the hook body and 11 mm in height. The open area of the body is tapped (9.0 mm diameter) in the middle, where the 10 mm screw is placed. The top of the back view shows the blade (FIG. 3, label M) of the thoracic lamina hook measuring 5.0 mm side to side with the edges rounded (1.0 mm radius).

Figure 4:
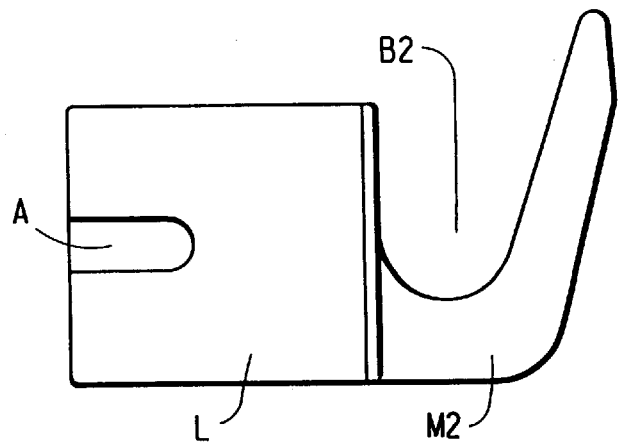
FIG. 4 shows a side view of a pedicle spinal hook.

FIG. 4 shows a side view of a pedicle hook used in the posterior spinal fixation system described in this patent application. The part of the pedicle hook labeled L is the body of the spinal hook and is the area measured from the back of the hook forward 12 mm towards the front of the hook and from the bottom of the hook up 11 mm towards the top of the hook. In this side view a ridge (FIG. 4, label A) flush with the back and 4.5 mm from the bottom and 4.5 from the top, with a width of 2.0 mm and a length of 5.0 mm projects out of the page, with the edge facing the front being rounded (1.0 mm radius). The part of the pedicle hook labeled M2 is the blade of the spinal hook and is the area measured from the front of the hook backwards 9.5 mm towards the back of the hook and ends where the body of the hook begins, and from the bottom of the hook up 15 mm towards the top of the hook. In this side view the open area (FIG. 4, label B2) of the blade is seen having a depth of 7.5 mm, rounded at the bottom (radius 3.0 mm) with a slope of 105 degrees from the front top edge of the hook to edge of the open area's rounded bottom.

Figure 5:
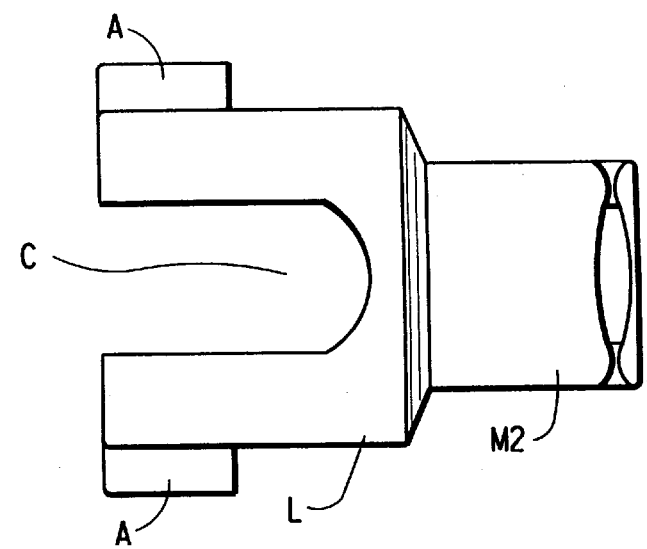
FIG. 5 shows a top view of a pedicle spinal hook.

In FIG. 5 the top view of the pedicle hook is illustrated. In this top view the body (FIG. 5, label L) of the hook is 18 mm measured from side to side by 12 mm measured from front to back. The ridge (FIG. 5, label A) of metal in this view is seen on both sides of the hook and measures 2.0 mm from side to side and 5.0 mm from back to front. In this side view the open area of the body is seen having a depth of 11 mm measured back to front, and width 6.0 mm measured side to side, rounded at the bottom (radius 3.0 mm). The open area (FIG. 5, label C) of the body from the back to the front (7.0 mm deep) is tapped for the placement of a 10 mm fine threaded screw. The width of the blade (FIG. 5, label M2) is 9.5 mm measured side to side, and increases 2.25 mm per side as it nears (1.0 mm) the hook body.

Figure 6:
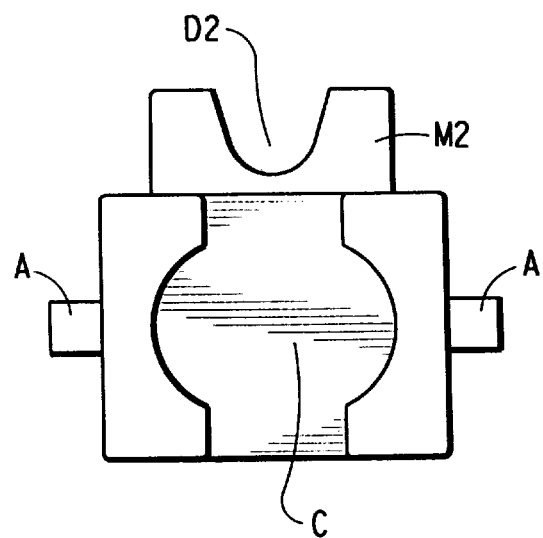
FIG. 6 shows a back view of a pedicle spinal hook.

In FIG. 6 the back view of the pedicle hook is illustrated. The body measured from the bottom to the top is 11.0 mm and the width measured from side to side is 18.0 mm. The 2.0 mm by 2.0 mm ridges (FIG. 6, label A) on this view are not rounded. The open area (FIG. 6, label C) of the body is seen and measures 6.0 mm in width at the top and bottom of the hook body and 11 mm in height. The open area of the body is tapped (9.0 mm radius) in the middle, where the 10 mm screw is placed. The top of the back view shows the blade (FIG. 6, label M2) of the pedicle hook measuring 9.5 mm side to side with the edges rounded and a groove (FIG. 6, label D2) for the pedicle to fit. The groove for the pedicle is 3.5 mm deep and rounded at the bottom with a 2.0 mm radius.

Figure 7:
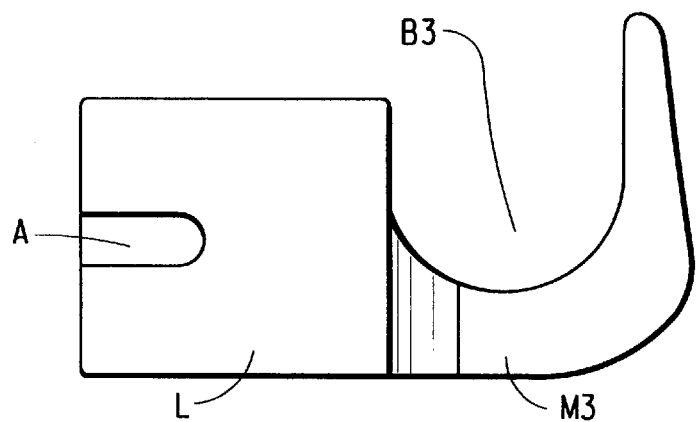
FIG. 7 shows a side view of a lamina spinal hook.

The blade (FIG. 7, label M3) of the lamina hook in FIG. 7 is the area measured from the front of the hook backwards 12.0 mm towards the back of the hook and ends where the body (FIG. 7, label L) of the hook begins, and from the bottom of the hook up 15 mm towards the top of the hook. In this side view a ridge (FIG. 7, label A) flush with the back and 4.5 mm from the bottom and 4.5 from the top, with a width of 2.0 mm and a length of 5.0 mm projects out of the page, with the edge facing the front being rounded (1.0 mm radius). In this side view the open area (FIG. 7, label B3) of the blade is seen having a depth of 10.0 mm, rounded at the bottom (radius 5.0 mm). The bottom front of the blade is rounded (radius 8.5 mm) and the top front of the blade is rounded.

Figure 8:
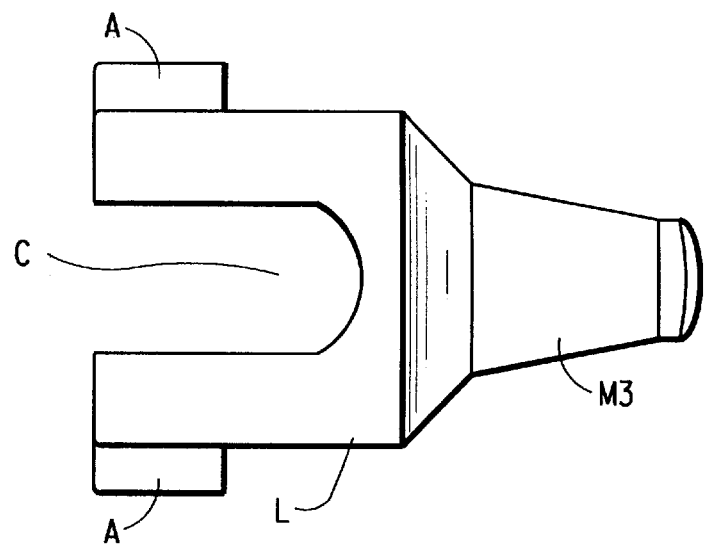
FIG. 8 shows a top view of a lamina spinal hook.

In FIG. 8 the top view of the lamina hook is illustrated. In this top view the body (FIG. 8, label L) of the hook is 18 mm measured from side to side by 12 mm measured from front to back. The ridge of metal (FIG. 8, label A) in this view is seen on both sides of the hook and measures 2.0 mm from side to side and 5.0 mm from back to front. In this side view the open area (FIG. 8, label C) of the body is seen having a depth of 11 mm measured back to front, and width 6.0 mm measured side to side, rounded at the bottom (radius 3.0 mm). The open area of the body is tapped from the back to the front (7.0 mm deep) for the placement of a 10 mm wide fine threaded screw. The width of the blade (FIG. 8, label M3) is 5.0 mm measured side to side at the front of the hook and increases to 8.0 mm in a distance of 7.5 mm and then the blade increases further to 14 mm in distance of 2.5 mm, with the front face of the blade being rounded. The length of the blade is 12.0 mm.

Figure 9:
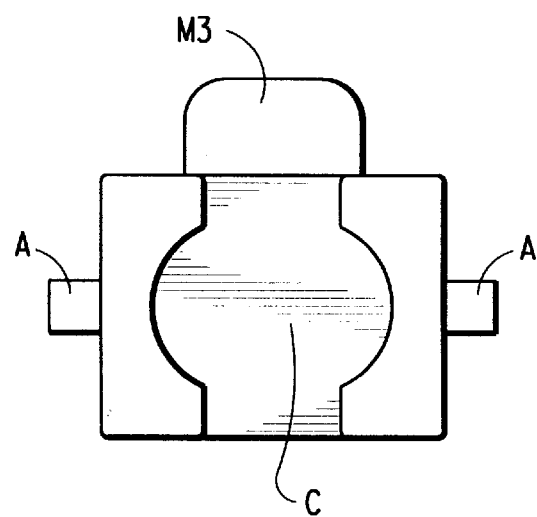
FIG. 9 shows a back view of a lamina spinal hook.

In FIG. 9 the back view of the lamina hook is illustrated. The body measured from the bottom to the top is 11.0 mm and the width measured from side to side is 18.0 mm. The 2.0 mm by 2.0 mm ridges (FIG. 9, label A) on this view are not rounded. The open area (FIG. 9, label C) of the body is seen and measures 6.0 mm in width at the top and bottom of the hook body and 11 mm in height. The open area of the body is tapped (9.0 mm diameter) in the middle, where the 10 mm screw is placed. The top of the back view shows the blade (FIG. 9, label M3) of the lamina hook measuring 5.0 mm side to side with the edges rounded (2.0 mm radius).

All of the spinal hooks described in this patent application can be made of stainless steel and or titanium that is of a grade which is approved for use in humans. Also all blades of the spinal hooks can vary in width and height in order to address all anatomic variants encountered in the human spine.

Figure 10:
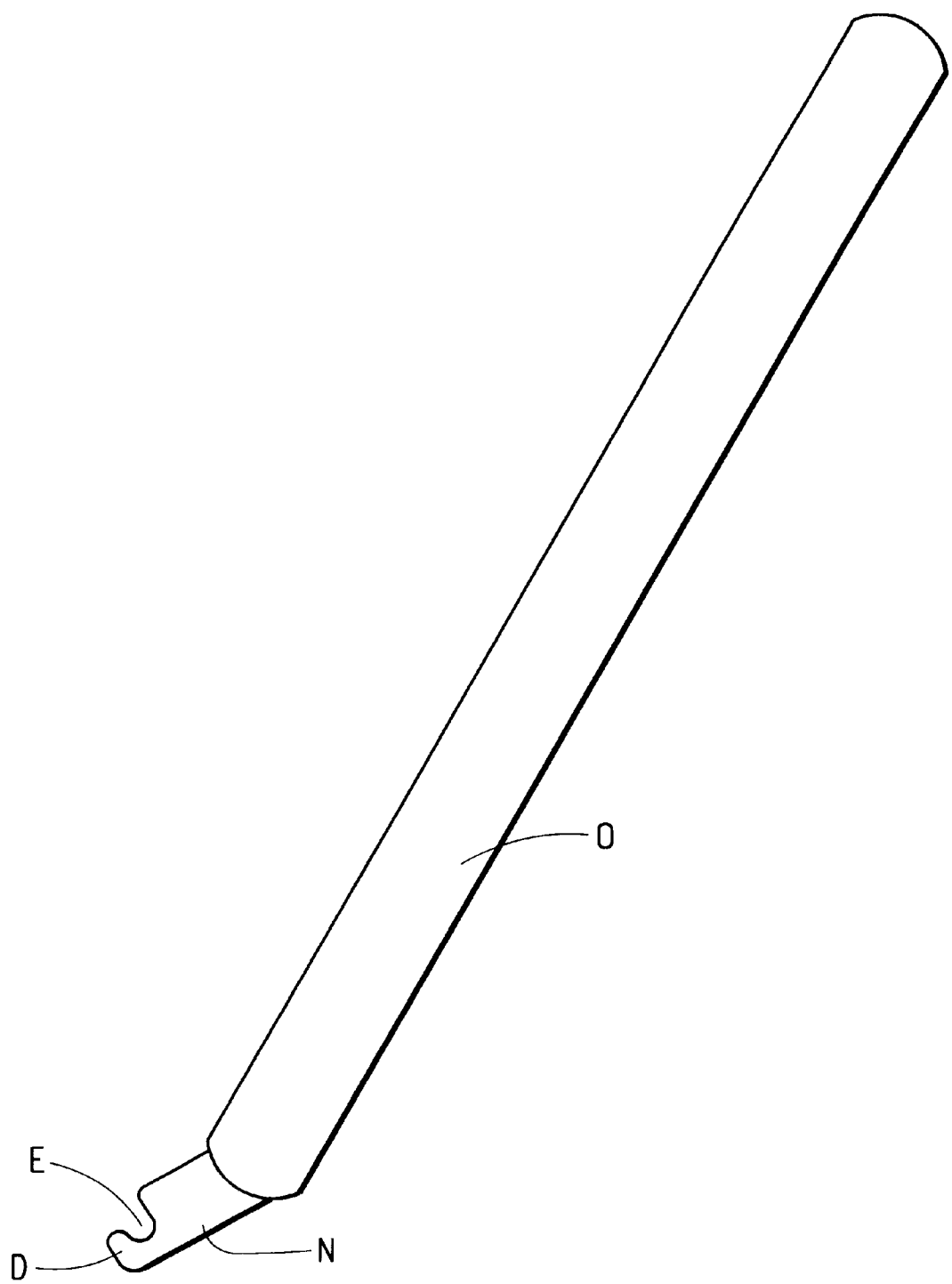
FIG. 10 shows a side view of the tool used for securing the spinal hooks to the rod.

In FIG. 10, the side view of the reduction tool, used for bringing the rod to the hook, is illustrated. The end which mates with the hook body is labeled N. The mating end is 26 mm wide and 15 mm high where the lever arm handle is attached. The lever arm (FIG. 10, label O) of the reduction tool serves as a handle to manipulate the tool. The hook shaped configuration (FIG. 10, label D) on the mating end of the tool has a 5.5 mm width is 12.5 mm in height and is rounded on the bottom (radius 11.0). The open area (FIG. 10, label E) is 6.5 mm wide 7.0 mm deep and is rounded at the bottom (radius 3.25). The open area is designed to mate with the metal ridge on the hook bodies previously described in FIGS. 1–9 and labeled a. The lever arm handle is 20.0 mm wide and 280.0 mm long. The long axis is a angled 25 degrees counterclockwise from the bottom of the mating end of the tool.

Figure 11:
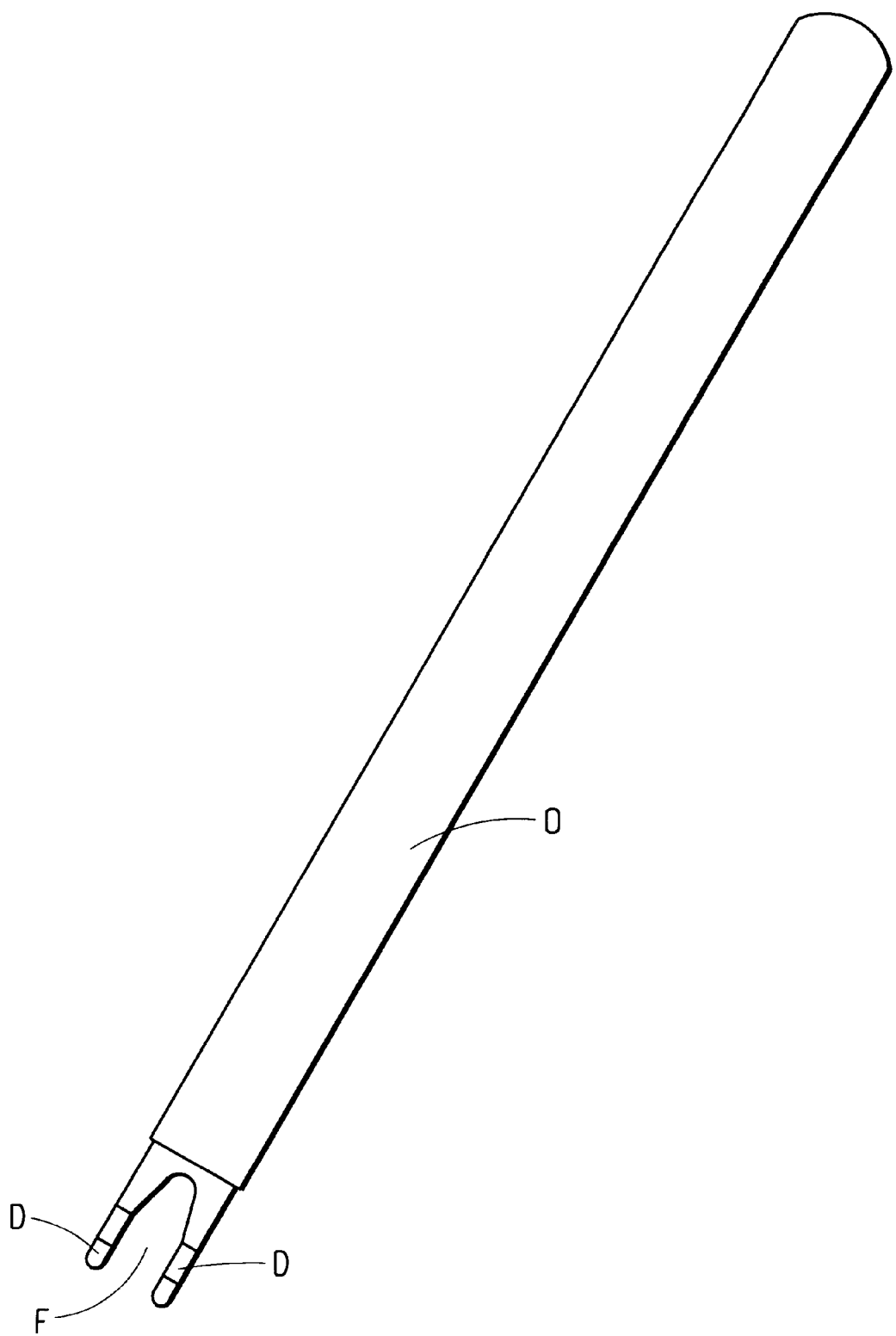
FIG. 11 shows a top view of the tool used for securing the spinal hooks to the rod.

In FIG. 11 the top view of the reduction tool, used for bringing the rod to the hook body, is illustrated. The mating end of the tool in this view measures 20.25 mm in width and 26 mm in height. The hook shaped configuration (FIG. 11, label D) on the mating end of the tool has a 3.0 mm width in this view. The open space (FIG. 11, label F) seen in this view is 14.25 mm wide and 14 mm in height in order to fit a hook in the middle of the elements labeled D. The open space begins to taper to a width of 6.0 mm at 14 mm from the edge of the mating end and is rounded at the bottom (radius 3.0 mm). The length of the lever arm handle (FIG. 11, label O) is 280 mm. This tool should be made of a corrosive resistant tool steel, and the length of the lever arm handle may also vary.

Figure 12A:
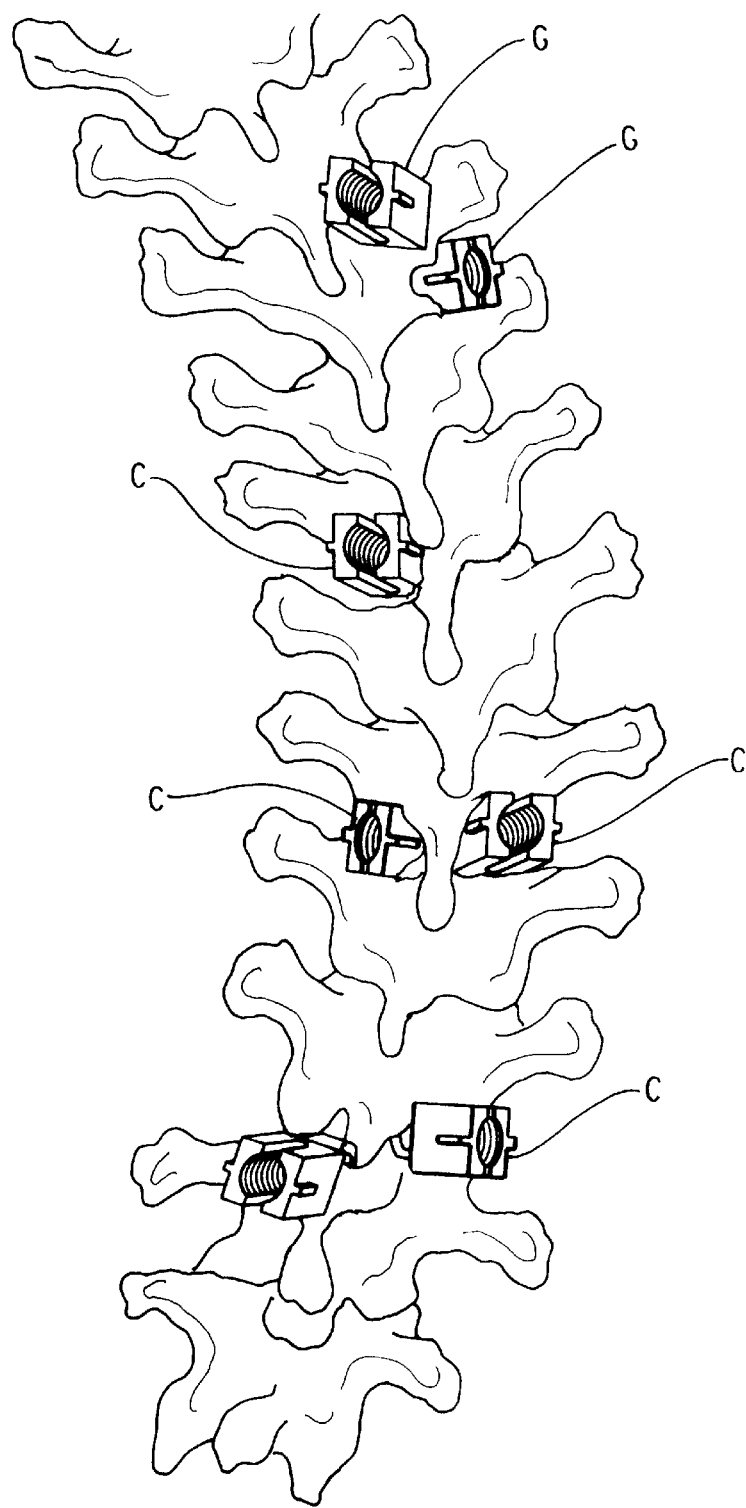
FIG. 12a shows a top view of the spine with several spinal hooks inserted.

In FIG. 12A, a top view of the spine, the spinal hooks (FIG. 12A, label G) inserted into the spine is illustrated. Note the open spaces in the body of the hooks(FIG. 12A, label C), this is where the rod will be placed and the 10 mm fine threaded screw will be secured.

Figure 12B:
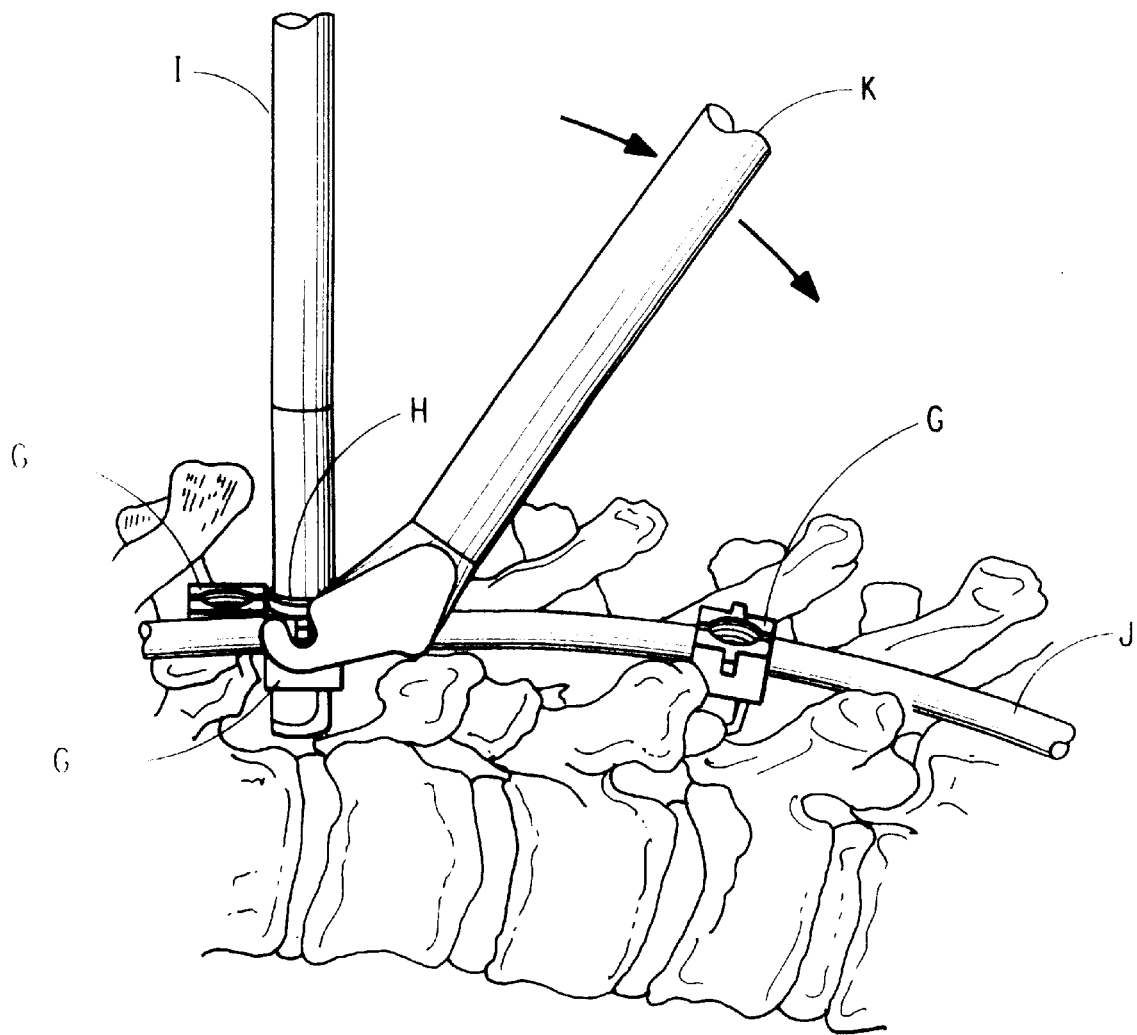
FIG. 12b shows a perspective view of the spine with the hooks being secured.

In FIG. 12B, a perspective view of the spine, the spinal hooks (FIG. 12B, label G), screw (FIG. 12B, label H), screwdriver (FIG. 12B, label I), spinal rod (FIG. 12B, label J) and tool (FIG. 12B, label K) for bringing the rod to the hook are illustrated as would be used in spinal surgery. The spinal hook dimensions follow those already described in earlier figures. The set screw is a standard 10 mm fine thread. The head of the screwdriver is a standard hexagonal dimension that fits the screw, with the bottom half is illustrated. The spinal rod is 5.5 mm in diameter and the length of the rod varies according to the length required for the spine fusion. The dimensions for the tool used to bring the rod to the hook follow those described in previous figures.

Figure 13A:
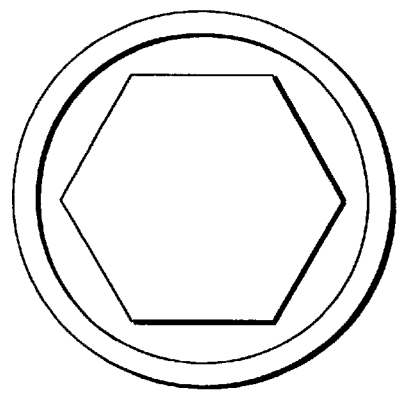
FIG. 13a shows a top view of the set screw.

In FIG. 13A the top view of the set screw is illustrated. In this top view a hexagonal opening (FIG. 13, label P) delineates the area into which a hexagonal headed screwdriver is placed.

Figure 13B:
FIG. 13b shows a side view of the set screw.

In FIG. 13B the side view of the set screw is illustrated. In this side view the fine thread is illustrated.

Figure 14:
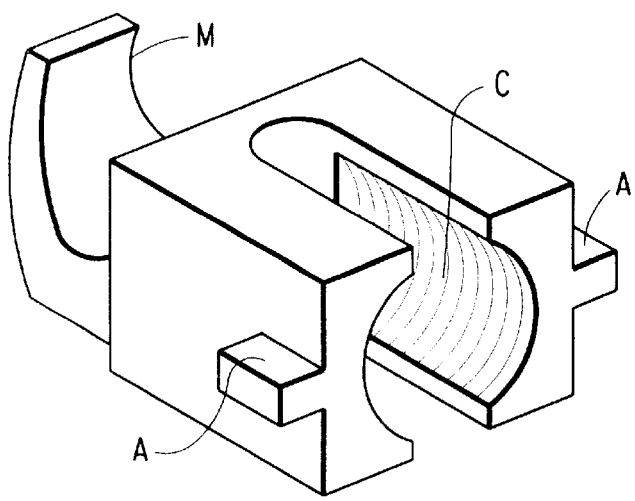
FIG. 14 shows a perspective view of the spinal hook.

In FIG. 14 a perspective view of the spinal hook is illustrated. In this view the relationship of the ridges (FIG. 14, label A) to the open area (FIG. 14, label C) which receives the spinal rod and the blade (FIG. 14, label M) of the spinal hook is illustrated.

Figure 15:
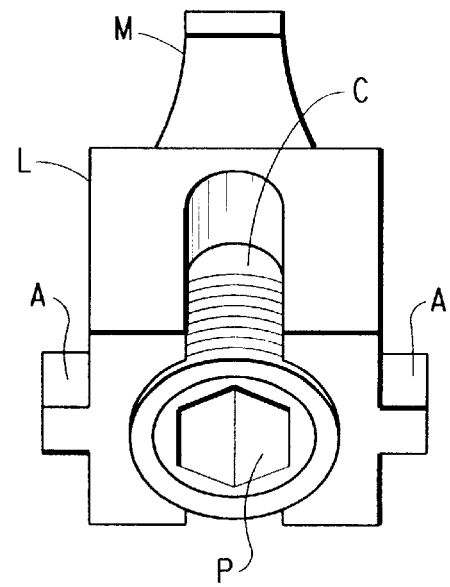
FIG. 15 shows a perspective view of the spinal hook wit a set screw in place.

In FIG. 15 a perspective view of the spinal hook with a set screw in place is illustrated. In this view the relationships of the ridges (FIG. 15, label A) to the open area (FIG. 15, label C) which receives the spinal rod and the body (FIG. 15, label L) and blade (FIG. 15, label M) of the spinal hook are illustrated. The set screw can be distinguished by noting its hexagonal opening (FIG. 15, label P) into which the hexagonal headed screwdriver is placed.

Operation—FIGS. 10, 11, 12a and 12b

The operation of this spinal fixation system will be described as used in the implantation into the human spine. It will not include the correction of the deformity, but rather only the insertion of the newly designed spinal hooks and instruments.

After the deformed spine is surgically exposed and the sites of spinal hook placement are prepared, the hooks should be inserted in the spine. Depending on the area of the spine and the anatomic variations found the surgeon should insert the specific hook which fits best. In FIG. 12A the illustration shows the hooks (FIG. 12A, label G) in place.

In FIG. 12B the illustration is a perspective view of the spinal fixation system. After the hooks (FIG. 12B, label G) are placed and the spinal rod is laid over the hooks, the reduction tool (FIG. 12B, label K) for brining the rod to the hook is inserted such that the spinal rod is in between the hook shaped configurations(FIGS. 10, 11, label D) and that the open areas (FIG. 10, label E) of the tool mate with the ridges of the body of the spinal hook (FIG. 12B, label G). Then the tool is pushed down and through a lever action the rod becomes seated in the open area (FIG. 12A, label C) of the body of the spinal hook. When the tool is pushed all the way down as illustrated in FIG. 12B (label K), the spinal rod is well seated in the open area of the hook body. This allows access to the tapped area of the hook. With this access, the screw (FIG. 12B, label H) is placed with the screwdriver (FIG. 12B, label I) in order to secured the rod (FIG. 12B, label J). The process described is then repeated for each hook, after which the scoliotic curve may be corrected and the patient's surgical incision closed, with the instrumentation left in place until the surgeon deems it necessary to remove.

Summary, Ramifications and Scope

The are several variations of the above spinal instrumentation which may be employed.

All of the spinal hooks described in this patent application may be made of stainless steel and or titanium that is of a grade which is approved for use in humans, further various strengths of the metals may also be used.

All of the spinal hooks may vary in width, height or angle in order to address all anatomic variants encountered in the human spine. The variations can be any degree as long as the hook body retains adequate ridges of metal which allow the mating of the tools to the hooks.

The metal ridges may also be changed in width, height or length to accommodate different tools or anatomic locations.

The handles of all tools may also be changed in width, height or angle in order to accommodate the different hand sizes and preferences of the surgeons who use this system. The angle of the handle to the mating end of the reduction tool may be changed. The sizes of the mating end of the tool may be changed to accommodate different sized hooks.

The spinal rod also may vary in metal type, strength and length.

Having described specific preferred embodiments of the invention, the following is claimed:

1. A spinal fixation device comprising
   (a) a body comprising
      (1) a base;
      (2) a block extending from the base to define a central, open ended, U-shaped channel having a straight trough defining a trough axis, an open top directed away from the base and oppositely facing inside walls having female screw threads adapted to mate with a male threaded set screw aligned perpendicular to the trough axis; and
      (3) a hook adjoining the base adapted to engage crevices of a vertebrate spine; and
   (b) a removable set screw having male screw threads adapted to mate with the female screw threads;
      in which the block further comprises two oppositely facing outside walls parallel to the trough axis, and a ridge protruding from each outside wall, and
      in which the outside walls have a width defined in the direction parallel to the trough axis and the ridge extends in the direction parallel to the trough axis for a distance less than the width.

2. The spinal fixation device of claim 1 in which each ridge comprises a lever support surface facing the base.

3. The spinal fixation device of claim 1 in which the lever support surface is convexly curved.

4. The spinal fixation device of claim 3 in which the lever support surface is semicircular.

5. The spinal fixation device of claim 1 in which the ridge is disposed centrally along the width on each outside wall.

* * * * *

UNITED STATES PATENT AND TRADEMARK OFFICE
CERTIFICATE OF CORRECTION

PATENT NO : 5,944,720
DATED : August 31, 1999
INVENTOR(S): Glenn E. Lipton

It is certified that error appears in the above-identified patent and that said Letters Patent is hereby corrected as shown below:

In column 8, line 27, delete " 1 in which the lever " and substitute -- 2 in which the lever -- therefor.

Signed and Sealed this

First Day of February, 2000

Attest:

Q. TODD DICKINSON

Attesting Officer

Acting Commissioner of Patents and Trademarks